United States Patent [19]

Hamaguchi et al.

[11] Patent Number: 4,863,504

[45] Date of Patent: Sep. 5, 1989

[54] CYCLOHEXADIONE DERIVATIVES, SELECTIVE HERBICIDAL COMPOSITIONS AS WELL AS HERBICIDAL METHOD

[75] Inventors: Hiroshi Hamaguchi, Kyoto; Tetsuji Ohshima; Eiji Kohno, both of Nishinomiya; Hideo Takaishi, Tokyo; Tsutomu Mabuchi; Katsumasa Okawa, both of Kawachinagano, all of Japan

[73] Assignee: Nihon Nohyaku Co., Ltd., Tokyo, Japan

[21] Appl. No.: 186,436

[22] Filed: Apr. 26, 1988

[30] Foreign Application Priority Data

Apr. 27, 1987 [JP] Japan ................................ 62-103731
Oct. 24, 1987 [JP] Japan ................................ 62-269113
Jan. 29, 1988 [JP] Japan ................................ 63-18616
Apr. 14, 1988 [JP] Japan ................................ 63-92309

[51] Int. Cl.$^4$ ............... A01N 43/56; C07D 231/12
[52] U.S. Cl. .......................................... 71/92; 548/378
[58] Field of Search .......................... 548/378; 71/92

[56] References Cited

FOREIGN PATENT DOCUMENTS 0066195 8/1982 European Pat. Off. .

Primary Examiner—Robert W. Ramsuer
Attorney, Agent, or Firm—Cushman, Darby & Cushman

[57] ABSTRACT

Novel cyclohexane-1,3-dione derivatives represented by 2-{1-(3-chloro-2-propenyloxyimino)propyl}-5-(1-methyl-1H-pyrazol-4-yl)cyclohexane-1,3-dione and intermediates thereof are disclosed. The cyclohexane-1,3-dione derivatives have a potent herbicidal effect against a wide variety of weeds and can selectively control injurous weeds at lower dosages. A process for preparing the cyclohexane-1,3-dione derivatives is also disclosed.

11 Claims, No Drawings

CYCLOHEXADIONE DERIVATIVES, SELECTIVE HERBICIDAL COMPOSITIONS AS WELL AS HERBICIDAL METHOD

FIELD OF THE INVENTION AND RELATED ART STATEMENT

The present invention relates to cyclohexane-1,3-dione derivatives represented by general formula (I):

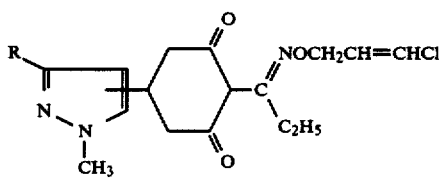

wherein R represents a hydrogen atom or a methyl group and the cyclohexane ring is substituted at the 4- or 5-position of the pyrazole ring, or salts thereof. The cyclohexane-1,3-dione derivatives or salts thereof in accordance with the present invention are novel compounds that are not found in publications. The present invention relates to these compounds or salts thereof, a process for preparing the same and use thereof as well as intermediate compounds for preparing the cyclohexane-1,3-dione derivatives.

It is described in Published Examined Japanese patent application KOKOKU No. 57-8099 and Published Unexamined Japanese patent application KOKAI (Laid-Open) Nos. 57-20035 and 62-4 that cyclohexane-1,3-dione are useful as herbicides. In particular, KOKAI No. 62-4 discloses an invention considered to be similar to the present invention.

SUMMARY OF THE INVENTION

However, the compounds of the present invention are not disclosed in the KOKAI publication supra at all but only some compounds considered to be similar are disclosed therein. In addition, a few compounds are provided with physical properties simply for specifying the disclosed compounds. Further there is found no description showing results that these compounds would be effective.

As a result of extensive investigations to find safe and novel herbicides having an enhanced herbicidal activity and having selectivity between useful plants and injurous weeds, the present inventors have found that the cyclohexane-1,3-dione derivatives or salts thereof represented by general formula (I) are novel compounds which have not been found in publications, exhibit a strong herbicidal activity against a wide variety of harmful weeds that are unexpectable from the KOKOKU publication supra and have safe and excellent selectivity of crops such as leguminous plants including soybeans, cottons, beets, sunflowers, etc. The inventors have thus accomplished the present invention.

DETAILED DESCRIPTION OF THE INVENTION

One aspect of the present invention lies in the cyclohexane-1,3-dione derivatives or salts thereof represented by general formula (I) described above.

Preferred are those of general formula (I) wherein R is H or CH$_3$.

As more preferred ones, mention may be made of the following specific compounds:

2-{1-(3-Chloro-2-propenyloxyimino)propyl}-5-(1-methyl-1H-pyrazol-4-yl)cyclohexane-1,3-dione,
2-{1-(3-Chloro-2-propenyloxyimino)propyl}-5-(1-methyl-1H-pyrazol-5-yl)cyclohexane-1,3-dione,
(E)-2-{1-(3-Chloro-2-propenyloxyimino)propyl}-5-(1-methyl-1H-pyrazol-4-yl)cyclohexane-1,3-dione,
(E)-2-{1-(3-Chloro-2-propenyloxyimino)propyl}-5-(1methyl-1H-pyrazol-5-yl)cyclohexane-1,3-dione,
2-{1-(3-Chloro-2-propenyloxyimino)propyl}-5-(1,3-dimethyl-1H-pyrazol-4-yl)cyclohexane-1,3-dione,
2-{1-(3-Chloro-2-propenyloxyimino)propyl}-5-(1,3-dimethyl-1H-pyrazol-5-yl)cyclohexane-1,3-dione,
(E)-2-{1-(3-Chloro-2-propenyloxyimino)propyl}-5-(1,3-dimethyl-1H-pyrazol-4-yl)cyclohexane-1,3-dione, and,
(E)-2-{1-(3-Chloro-2-propenyloxyimino)propyl}-5-(1,3-dimethyl-1H-pyrazol-5-yl)cyclohexane-1,3-dione.

Another aspect of the present invention lies in a process for preparing cyclohexane-1,3-dione derivatives represented by general formula (I):

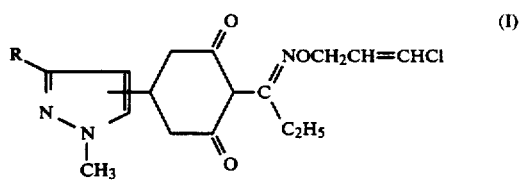

wherein R represents a hydrogen atom or a methyl group and the cyclohexane ring is substituted at the 4- or 5-position of the pyrazole ring, or salts thereof which comprises reacting compounds represented by general formula (II):

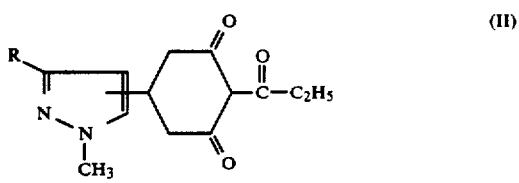

wherein R has the same significance as described above, with a compound represented by general formula (III):

$$Cl-CH=CH-CH_2-ONH_2 \qquad (III)$$

A third aspect of the present invention lies in intermediate compounds for preparing the cyclohexane-1,3-dione derivatives or salts thereof, which are represented by general formula (II-1):

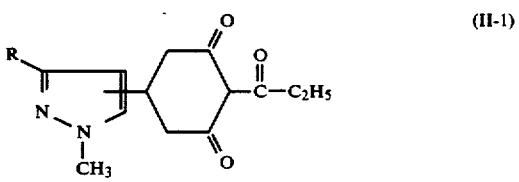

wherein R represents a hydrogen atom or a methyl group.

Of these, 5-(1-methyl-1H-pyrazol-5-yl)-2-propionyl-cyclohexane-1,3-dione and 5-(3-dimethyl-1H-pyrazol-5-yl)-2-propionylcyclohexane-1,3-dione are particularly useful as the intermediates.

A fourth aspect of the present invention resides in selective herbicidal compositions comprising cyclohexane-1,3-dione derivatives represented by general formula (I):

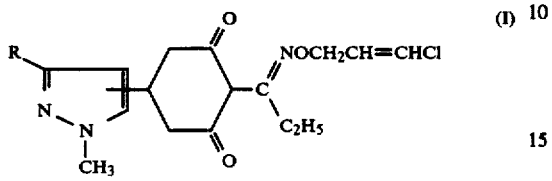

wherein R represents a hydrogen atom or a methyl group and the cyclohexane ring is substituted at the 4- or 5-position of the pyrazole ring, or salts thereof in a herbicidally effective dose and inert carriers. The herbicidal compositions can be preferably used particularly for dry field farming soybeans, more preferably for treatment at the growth stage of soybeans.

As the selective herbicides, the following compounds are advantageously used:

2-{1-(3-Chloro-2-propenyloxyimino)propyl}-5-(1-methyl-1H-pyrazol-4-yl)cyclohexane-1,3-dione,
2-{1-(3-Chloro-2-propenyloxyimino)propyl}-5-(1-methyl-1H-pyrazol-5-yl)cyclohexane-1,3-dione,
(E)-2-{1-(3-Chloro-2-propenyloxyimino)propyl}-5-(1-methyl-1H-pyrazol-4-yl)cyclohexane-1,3-dione,
(E)-2-{1-(3-Chloro-2-propenyloxyimino)propyl}-5-(1-methyl-1H-pyrazol-5-yl)cyclohexane-1,3-dione,
2-{1-(3-Chloro-2-propenyloxyimino)propyl}-5-(1,3-dimethyl-1H-pyrazol-4-yl)cyclohexane-1,3-dione,
2-{1-(3-Chloro-2-propenyloxyimino)propyl}-5-(1,3-dimethyl-1H-pyrazol-5-yl)cyclohexane-1,3-dione,
(E)-2-{1-(3-Chloro-2-propenyloxyimino)propyl}-5-(1,3-dimethyl-1H-pyrazol-4-yl)cyclohexane-1,3-dione, and,
(E)-2-{1-(3-Chloro-2-propenyloxyimino)propyl}-5-(1,3-dimethyl-1H-pyrazol-5-yl)cyclohexane-1,3-dione.

A fifth aspect of the present invention resides in a herbicidal method which comprises treating soybeans at the post-emergence stage with herbicidal compositions comprising cyclohexane-1,3-dione derivatives represented by general formula (I):

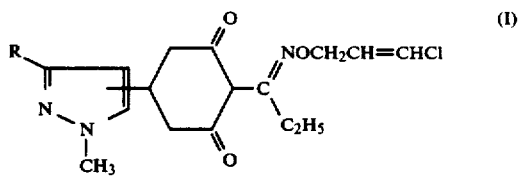

wherein R represents a hydrogen atom or a methyl group and the cyclohexane ring is substituted at the 4- or 5-position of the pyrazole ring, or salts thereof as effective components in a range of 1 g to 1000 g per hectare, thereby to protect soybean crops from undesired weeds.

As a preferred method, mention may be made of a treatment of soybeans using at least one of the following compounds:

2-{1-(3-Chloro-2-propenyloxyimino)propyl}-5-(1-methyl-1H-pyrazol-4-yl)cyclohexane-1,3-dione,
2-{1-(3-Chloro-2-propenyloxyimino)propyl}-5-(1-methyl-1H-pyrazol-5-yl)cyclohexane-1,3-dione,
(E)-2-{1-(3-Chloro-2-propenyloxyimino)propyl}-5-(1-methyl-1H-pyrazol-4-yl)cyclohexane-1,3-dione,
(E)-2-{1-(3-Chloro-2-propenyloxyimino)propyl}-5-(1-methyl-1H-pyrazol-5-yl)cyclohexane-1,3-dione,
2-{1-(3-Chloro-2-propenyloxyimino)propyl}-5-(1,3-dimethyl-1H-pyrazol-4-yl)cyclohexane-1,3-dione,
2-{1-(3-Chloro-2-propenyloxyimino)propyl}-5-(1,3)-dimethyl-1H-pyrazol-5-yl)cyclohexane-1,3-dione,
(E)-2-{1-(3-Chloro-2-propenyloxyimino)propyl}-5-(1,3-dimethyl-1H-pyrazol-4-yl)cyclohexane-1,3-dione, and,
(E)-2-{1-(3-Chloro-2-propenyloxyimino)propyl}-5-(1,3-dimethyl-1H-pyrazol-5-yl)cyclohexane-1,3-dione.

The cyclohexane-1,3-dione derivatives represented by general formula (I) or salts thereof and the compounds represented by general formula (II), which are intermediates for the compounds of formula (I), of the present invention involve tautomers illustrated below and the present invention also includes these tautomers.

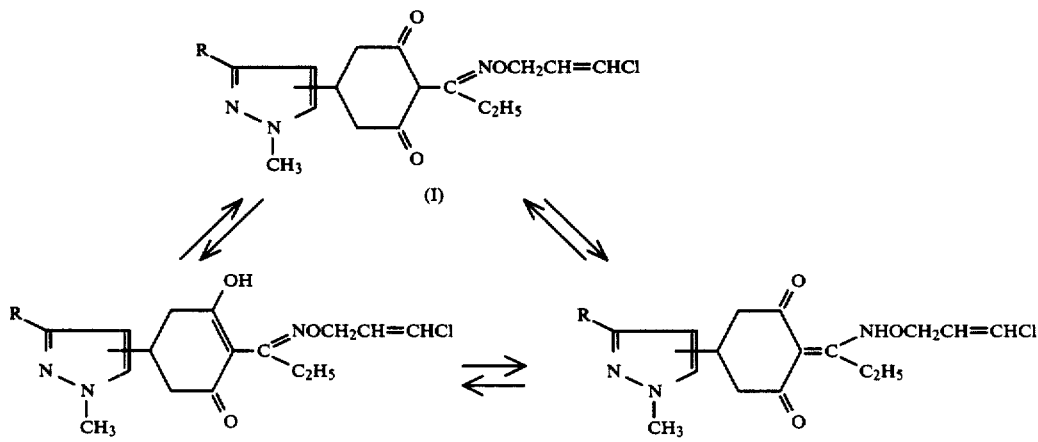

wherein R has the same significance as described above.

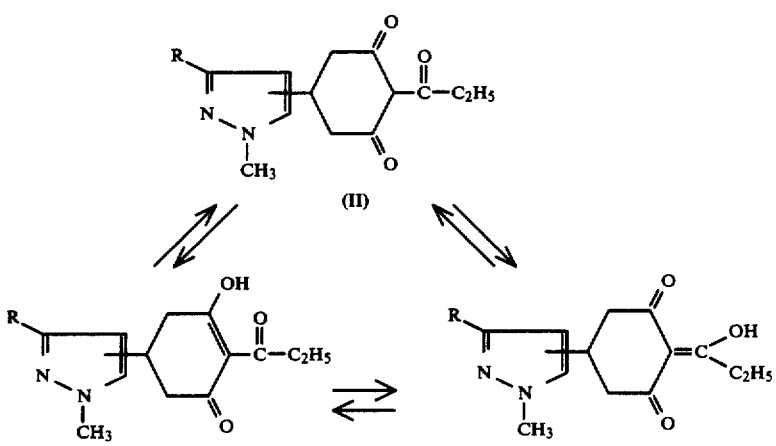

wherein R has the same significance as described above.

Further the cyclohexane-1,3-dione derivatives represented by general formula (I) or salts thereof of the present invention also posses E- Z-isomers and the present invention also includes these isomers. Of these isomers, the selective herbicidal activity is more potent in the E-isomers than in the Z-isomers.

Examples of the salts of cyclohexane-1,3-diode derivatives represented by general formula (I) of the present invention include salts of alkali metals such as potasssium, sodium, etc. and in addition, salts of manganese, copper, zinc, iron, barium, and the like.

A representative example of the process for preparing the cyclohexane-1,3-dione derivatives or salts thereof of the present invention can be illustratively shown below:

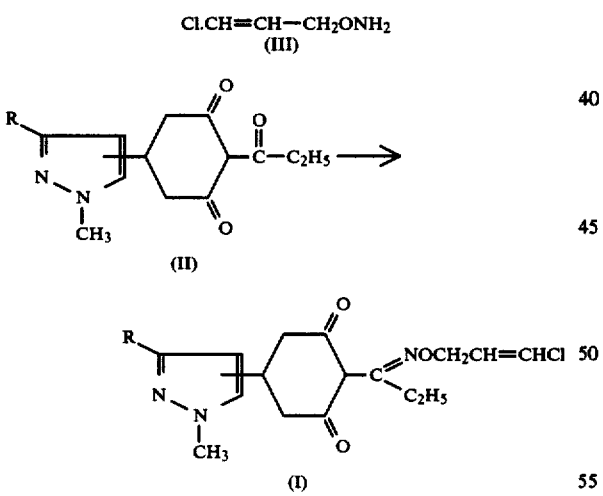

wherein R has the same significance as described above.

Namely, the cyclohexane-1,3-dione derivatives represented by general formula (I) or salts thereof of the present invention can be prepared by reacting the compounds represented by general formula (II) with the compound represented by general formula (III) in the presence of inert solvents.

As the inert solvents which can be used in the reaction, any solvent may be used as far as they do not seriously disturb the progress of reaction. Examples of such inert solvents include alcohols such as methanol, ethanol, propanol, cyclohexanol, etc.; chlorinated hydrocarbons such as methylene chloride, dichloromethane, chloroform, carbon tetrachloride, etc.; aromatic hydrocarbons such as benzene, toluene, xylene, etc.; esters such as ethyl acetate, etc.; nitriles such as acetonitrile, etc.; cyclic ethers such as dioxane, tetrahydrofuran, etc.

The reaction is an equimolar reaction and the reactants can be used in equimolar amounts, but either the compounds represented by general formula (II) or the compound represented by general formula (III) may be used in an excess amount.

The reaction temperature may be chosen in the range of from 0° C. and 50° C.

The reaction time varies depending upon amount of reactants and reaction temperature but may be any time period as far as the reaction is completed, and can be chosen from the range of several minutes to 48 hours.

After completion of the reaction, the reaction products may be isolated in a conventional manner. The objective cyclohexane-1,3-dione derivatives represented by general formula (I) or salts thereof can be obtained by treating the reaction product, for example, by means of extraction with a solvent, etc. and if necessary, by purifying through dry column chromatography, recrystallization, etc.

Next, a representative example of the process for preparing the compounds represented by general formula (II), which are intermediates for preparing the cyclohexane-1,3-dione derivatives represented by general formula (I) or salts thereof of the present invention, can be illustratively shown below:

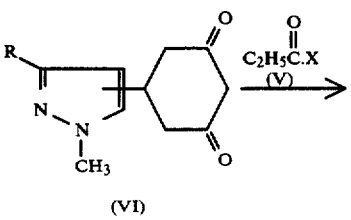

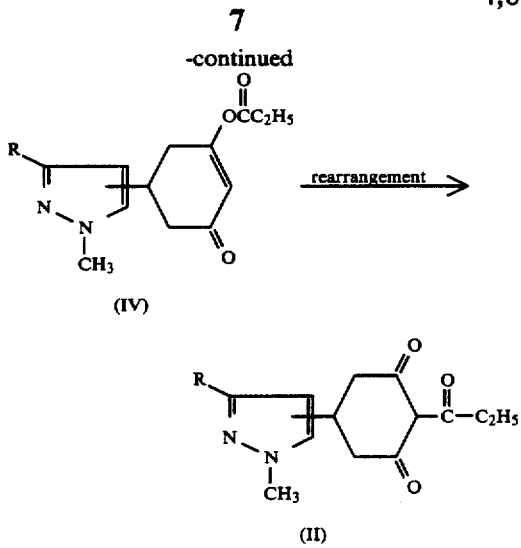

wherein R has the same significance as described above and X represents a halogen atom.

Namely, the compounds represented by general formula (II) can be prepared by reacting the compounds represented by general formula (VI) with the compounds represented by general formula (V) in the presence of bases in the presence or absence of inert solvents to produce the compounds represented by general formula (IV) and, subjecting the compounds (IV) to rearrangement in the presence of catalysts, with or without isolating the compounds (IV).

As the inert solvents which can be used at the first step of reaction, any solvents may be used as far as they do not seriously disturb the progress of reaction. Examples of such inert solvents include chlorinated hydrocarbons such as methylene chloride, dichloromethane, chloroform, carbon tetrachloride, etc.; aromatic hydrocarbons such as benzene, toluene, xylene, etc.; esters such as ethyl acetate, etc.; nitriles such as acetonitrile, etc.; chain ethers such as methyl cellosolve, diethyl ether, etc.; cyclic ethers such as dioxane, tetrahydrofuran, etc.

The reaction is an equimolar reaction and the reactants can be used in equimolar amounts, but the compounds represented by general formula (V) may be used in an excess amount.

As bases that can be used in the reaction, mention may be made of inorganic bases and organic bases. Examples of the inorganic bases include hydroxides, carbonates or alcoholates of alkali metals or alkaline earth metals such as sodium, potassium, magnesium, calcium, etc. Examples of the organic bases include triethylamine, pyridine, etc. The base may be used in an equimolar amount or in an excess amount based on the compounds represented by general formula (VI).

The reaction temperature may be chosen in the range of from 0° C. to the boiling point of a solvent, preferably in the range between 10° C. and 50° C.

The reaction time varies depending upon amount of reactants and reaction temperature but may be any time period as far as the reaction is completed, and can be chosen from the range of several minutes to 48 hours.

After completion of the reaction, the compounds represented by general formula (IV) may be used in the next reaction without isolating the same. Alternatively, the compounds may also be isolated from the reaction mixture in a conventional manner, by treating the compounds, for example, by means of extraction with a solvent, etc. and if necessary, by purifying through dry column chromatography, recrystallization, etc., thereby to give the objective compounds represented by general formula (IV). The compounds (IV) may also be isolated and provided for the next reaction.

As the inert solvents which can be used in the rearrangement of the second step of reaction, any solvents may be used as far as they do not seriously disturb the progress of reaction. Examples of such inert solvents include chlorinated hydrocarbons such as methylene chloride, dichloromethane, chloroform, carbon tetrachloride, etc.; aromatic hydrocarbons such as benzene, toluene, xylene, etc.; esters such as ethyl acetate, etc.; nitriles such as acetonitrile, benzonitrile, etc.; chain ethers such as methyl cellosolve, diethyl ether, etc.; cyclic ethers such as dioxane, tetrahydrofuran, etc.

As the catalyst that can be used in the rearrangement, mention may be made of, for example, 4-N,N-dimethylaminopyridine, acetone cyanhydrin, KCN, NaCN, etc. An amount of the catalyst to be used may be chosen from the range of 0.001 to 10 mols, preferably from the range of 0.1 to 1 mol, based on 1 mol of the compounds represented by general formula (IV). Further in the case of performing the rearrangement without isolating the compounds represented by general formula (IV), the catalyst may be used in the amount described above, based on the compounds represented by general formula (VI).

The reaction temperature may be chosen in the range of from room temperature to the boiling point of a solvent. The reaction can be preferably carried out with heating.

The reaction time varies depending upon amount of reactants and reaction temperature but may be any time period as far as the reaction is completed, and can be chosen from the range of several minutes to 48 hours.

After completion of the reaction, the reaction product may be isolated in a conventional manner, by treating the same, for example, by means of extraction with a solvent, etc. and if necessary, by purifying through column chromatography, recrystallization, etc., thereby to give the objective cyclohexanedione derivatives represented by general formula (I). Further, the cyclohexanedione derivatives represented by general formula (I) can also be treated with appropriate bases to give the salts thereof.

Representative examples of the cyclohexanedione derivatives represented by general formula (I) or salts thereof of the present invention and the compounds represented by general formula (II), which are intermediate compounds for producing these compounds, are given in Tables 1 and 2, respectively, but the present invention is not deemed to be limited thereto.

General Formula (I)

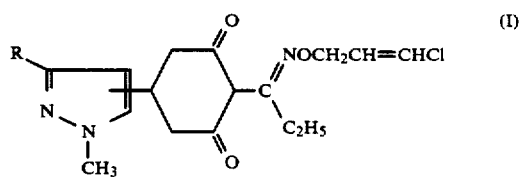

TABLE 1

| Compound | R | Substituted position on the cyclohexane ring | Physical properties |
|---|---|---|---|
| 1. | H | 4-position | mp. 99° C. (E-isomer) |
| 2. | H | 5-position | $\eta_D$ 1.5611 (13.1° C.) (E-isomer) |
| 3. | CH$_3$ | 4-position | mp. 100.1° C. (E-isomer) |
| 4. | CH$_3$ | 5-position | mp. 83–85° C. (E-isomer) |

General Formula (II)

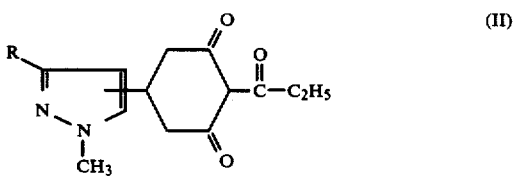

(II)

TABLE 2

| Compound No. | R | Substituted position on the cyclohexane ring | Physical properties |
|---|---|---|---|
| 5. | H | 5-position | mp. 85.2° C. |
| 6. | CH$_3$ | 5-position | $\eta_D$ 1.5331 (22.2° C.) |

The compounds represented by general formula (VI) can be prepared, for example, by methods as illustrated below.

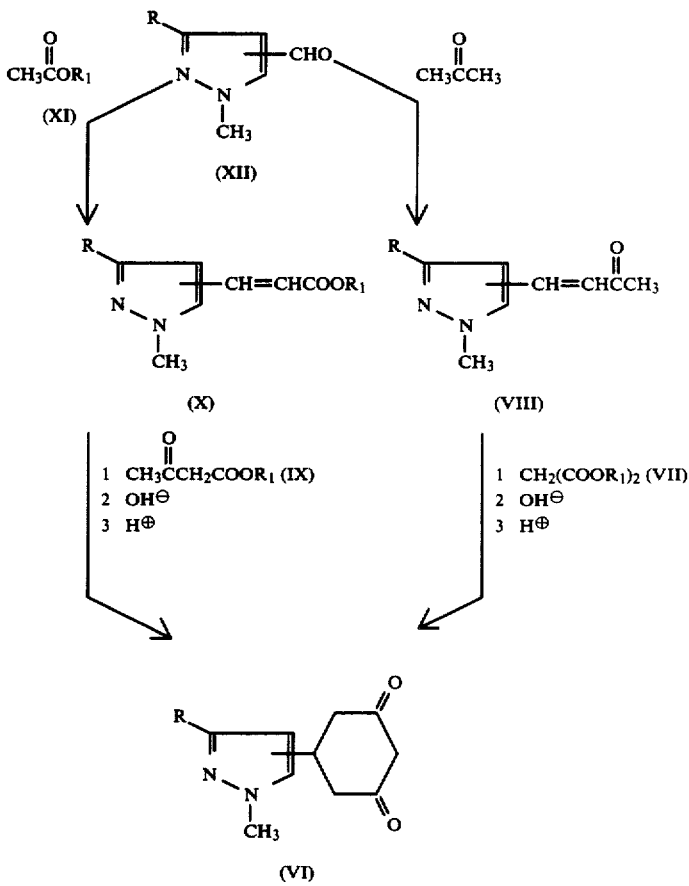

wherein R has the same significance as described above and R$_1$ represents a lower alkyl group.

That is, the compounds represented by general formula (VI) can be prepared by reacting the compounds represented by general formula (XII) with acetic acid esters represented by general formula (XI) to produce the compounds represented by general formula (X), reacting the compounds (X) with acetoacetates represented by general formula (IX) and then cyclizing the reaction products. Alternatively, the compounds represented by general formula (VI) can also be prepared by reacting the compounds represented by general formula (XII) with acetone to produce the compounds represented by general formula (VIII), reacting the compounds (VIII) with malonic acid esters represented by general formula (VII) and then cyclizing the reaction products.

Representative examples of the present invention are given below.

EXAMPLE 1

1. Preparation of 5-(1-methyl-1H-pyrazol-4-yl)-2-propionylcyclohexane-1,3-dione

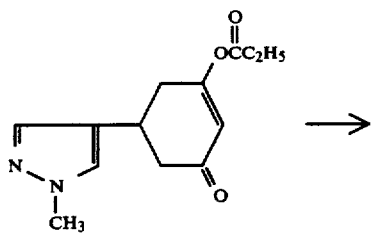

A mixture of 30.0 g (121 mmols) of 5-(1-methyl-1H-pyrazol-4-yl)-3-oxo-1-cyclohexenyl propionate and 7.4 g (61 mmols) of 4-N,N-dimethylaminopyridine was dissolved in 300 ml of tetrahydrofuran. The solution was heated to reflux for 5 hours to perform the reaction. After completion of the reaction, the reaction mixture was allowed to cool. The reaction solution was concentrated and the product was extracted with chloroform. Water was added to the extract and the aqueous phase was adjusted to pH of 4 to 5. The 4-N,N-dimethylaminopyridine was removed. After washing the chloroform phase with water and drying, the solvent was distilled off under reduced pressure to give 25.0 g of the product.

Melting point, 78° C.; Yield, 83%.

$^1$H NMR (CDCl$_3$, TMS), ppm.

δ1.12 (3H, t, J=7 Hz) 2.4–3.7 (7H, m) 3.83 (3H, s) 7.16 (1H, s) 7.29 (1H, s).

2. Preparation of (E)-2-[1-(3-chloro-2-propenyloxyimino)propyl]5-(1-methyl-1H-pyrazol-4-yl)cyclohexane-1,3-dione (Compound No. 1)

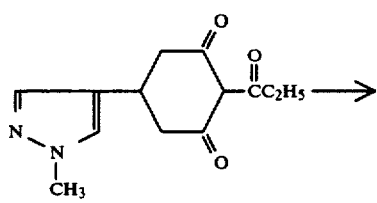

To 200 ml of an ethanolic solution of 20.0 g (81 mmols) of 5-(1-methyl-1H-pyrazol-4-yl)-2-propionylcyclohexane-1,3-dione was added 210 ml (84 mmols) of 0.4 mol ethanolic solution of (E)-3-chloro-2-propenyloxyamine. The mixture was reacted for 8 hours with stirring. After completion of the reaction, the reaction mixture was concentrated under reduced pressure. The resulting crude product was purified by silica gel column chromatography (ethyl acetate) to give 12.5 g of the product.

Physical properties: Melting point, 99° C. Yield, 46%.

$^1$H NMR (CDCl$_3$, TMS), ppm.

δ1.13 (3H, t, J=7 Hz) 2.4–3.7 (7H, m) 3.83 (3H, s) 4.49 (2H, d, J=6 Hz) 5.9–6.5 (2H, m) 7.16 (1H, s) 7.29 (1H, s).

EXAMPLE 2

Preparation of (E)-2-[1-(3-chloro-2-propenyloxyimino)propyl]-5-(1-methyl-1H-pyrazol-5-yl)-cyclohexane-1,3-dione (Compound No. 2)

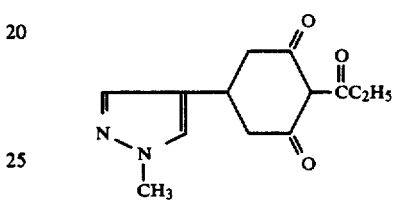

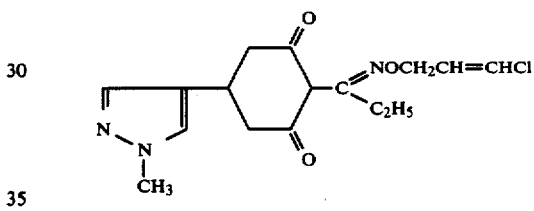

To 5 ml of an ethanolic solution of 0.35 g (1.4 mmols) of 5-(1-methyl-1H-pyrazol-5-yl)-2-propionylcyclohexane-1,3-dione was added 3.8 ml (1.4 mmols) of 0.38 mol ethanolic solution of (E)-3-chloro-2-propenyloxyamine. The mixture was reacted for 10 hours with stirring. After completion of the reaction, the reaction mixture was concentrated under reduced pressure. The resulting crude product was purified by silica gel column chromatography (hexane:ethyl acetate=b 1:2) to give 0.25 g of the product.

Physical properties: ηD 1.5611 (13.1° C.), Yield, 52.5%.

$^1$H NMR (CDCl$_3$, TMS), ppm.

δ1.14 (3H, t, J=7 Hz) 2.4–3.7 (7H, m) 3.83 (3H, s) 4.51 (2H, d, J=6 Hz) 6.02 (1H, d, J=2 Hz) 5.9–6.5 (2H, m) 7.35 (1H, , J=2 Hz).

EXAMPLE 3

1. Preparation of 5-(1,3-dimethyl-1-H-pyrazol-4-yl)-2-propionylcyclohexane-1,3-dione

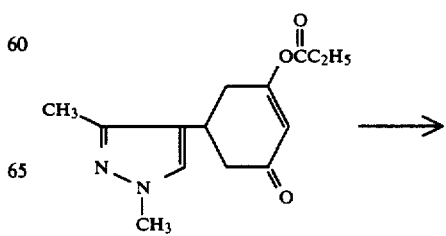

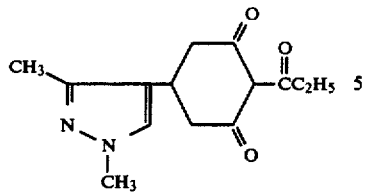

A mixture of 7.16 g (27.3 mmols) of 5-(1,3-dimethyl-1H-pyrazol-4-yl)-3-1-cyclohexenyl propionate and 1.0 g (8.2 mmols) of 4-N,N-dimethylaminopyridine was dissolved in 100 ml of tetrahydrofuran. The solution was heated to reflux for 6 hours to perform the reaction. After completion of the reaction, the reaction mixture was allowed to cool. The reaction liquid was concentrated under reduced pressure. The residue was poured into water and the aqueous phase was adjusted with diluted hydrochloric acid to pH of 5. The product was extracted with chloroform (100 ml×3). The extract was dried over anhydrous sodium sulfate and the extraction solvent was concentrated under reduced pressure to give 6.37 g of the product.

Physical properties: Melting point, 90°–91° C.; yield, 89.0%.

$^1$H NMR (CDCl$_3$, TMS), ppm.

δ1.15 (3H, t, J=7 Hz) 2.23 (3H,m) 2.25–3.5 (7H, m) 3.78 (3H, s) 7.03 (1H, s).

2. Preparation of (E)-2-[1-(3-chloro-2-propenyloxyimino)propyl]-5-(1,3-dimethyl-1H-pyrazol-4-yl)-cyclohexane-1,3-dione (Compound No. 3)

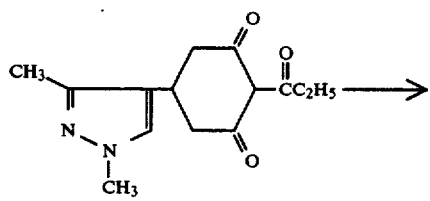

In 20 ml of ethanol was dissolved 2.62 g (10 mmols) of 5-(1,3-dimethyl-1H-pyrazol-4-yl)-2-propionylcyclohexane-1,3-dione and, 30 ml (12 mmols) of 0.4 mol ethanolic solution of (E)-3-chloro-2-propenyloxyamine was added to the solution. The mixture was reacted for 8 hours with stirring. After completion of the reaction, the reaction mixture was concentrated under reduced pressure. The resulting crude product was purified by silica gel column chromatography (chloroform:methanol=50:1) to give 3.21 g of the product.

Physical properties: Melting point, 100.1° C., Yield 91.2%.

$^1$H NMR (CDCl$_3$, TMS), ppm.

δ1.12 (3H, t, J=7 Hz) 2.20 (3H, s) 2.3–3.6 (7H, m) 3.75 (3H, s) 4.48 (2H, d, J=6 Hz) 5.8–6.6 (2H, m) 7.00 (1H, s).

EXAMPLE 4

Preparation of (E)-2-[1-(3-chloro-2-propenyloxyimino)propyl]-5-(1,3-dimethyl-1H-pyrazol-5-yl)cyclohexane-1,3-dione (Compound No. 4)

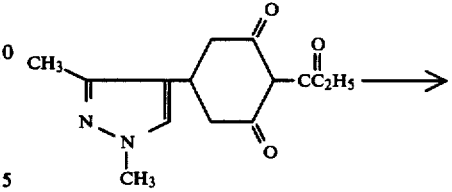

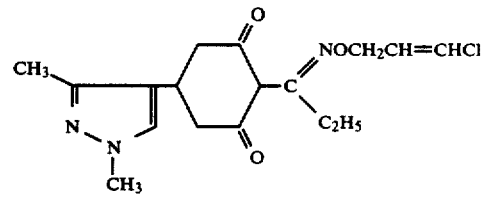

To 10 ml of a solution of 5.60 g (21.3 mmols) of 5-(1,3-dimethyl-1H-pyrazol-5-yl)-2-propionylcyclohexane-1,3-dione in methanol was added 57 ml (21.7 mmols) of 0.38 mol ethanolic solution of (E)-3-chloro-2-propenyloxyamine. The mixture was reacted for 10 hours with stirring. After completion of the reaction, the reaction mixture was concentrated under reduced pressure. The resulting crude product was purified by silica gel column chromatography (hexane:ethyl acetate=2:1) to give 6.84 g of the product.

Physical properties: Melting point, 83°–85° C., Yield, 91.1%.

$^1$H NMR (CDCl$_3$, TMS), ppm.

δ1.13 (3H, t, J=7 Hz) 2.16 (3H, s) 2.5–3.2 (6H, m) 3.2–3.7 (1H, m) 3.73 (3H, s) 4.51 (2H, d, J=6 Hz) 5.1 (1H, s) 5.9–6.5 (2H, m).

EXAMPLE 5

Preparation of 5-(1-methyl-1H-pyrazol-5-yl)-2-propionylcyclohexane-1,3-dione (Compound No. 5)

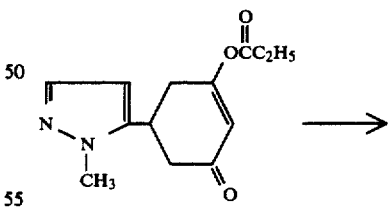

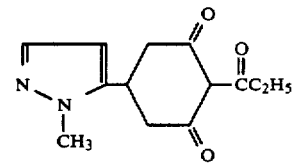

A mixture of 0.60 g (2.4 mmols) of 5-(1-methyl-1H-pyrazol-5-yl)-3-oxo-1-cyclohexane propionate and 0.1 g (0.8 mmols) of 4-N,N-dimethylaminopyridine was dissolved in 15 ml of tetrahydrofuran. The solution was heated to reflux for 20 hours to perform the reaction.

After completion of the reaction, the reaction mixture was allowed to cool. The reaction liquid was concentrated under reduced pressure. The resulting crude product was purified by silica gel column chromatography (hexane:ethyl acetate=1:2) to give 0.35 g of the product as an oily substance.

Physical properties: ηD 1.5387 (19.3° C.), Yield, 58.3%.

$^1$H NMR (CDCl$_3$, TMS), ppm.

δ1.12 (3H, t, J=7 Hz) 2.4–3.7 (7H, m) 3.78 (3H, s) 4.95 (1H, d, J=2 Hz) 7.25 (1H, d, J=2 Hz).

The obtained oily substance was allowed to stand, whereby the product was crystallized and obtained as crystals.

Physical properties: Melting point, 85.2° C., Data on $^1$H NMR was the same as in the oily substance.

EXAMPLE 6

Preparation of 5-(1,3-dimethyl-1H-pyrazol-5-yl)-2-propionylcyclohexane-1,3-dione (Compound No. 6)

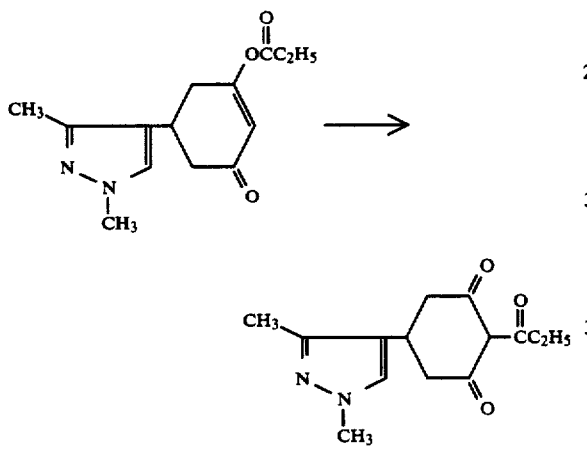

A mixture of 17.5 g (66.7 mmols) of 5-(1,3-dimethyl-1H-pyrazol-5-yl)-3-1-cyclohexenyl propionate and 0.85 g (7.0 mmols) of 4-N,N-dimethylaminopyridine was dissolved in 200 ml of tetrahydrofuran. The solution was heated to reflux for 2 hours to perform the reaction. After completion of the reaction, the reaction mixture was cooled. The reaction liquid was concentrated under reduced pressure. The resulting crude product was purified by silica gel column chromatography (hexane:ethyl acetate=2:1) to give 16.40 g of the product.

Physical properties: ηD 1.5331 (22.2° C.), Yield, 93.7%.

$^1$H NMR (CDCl$_3$, TMS), ppm.

67 1.15 (3H, t, J=7 Hz) 2.20 (3H, s) 2.4–3.6 (7H, m) 3.77 (3H, s) 5.82 (1H, s).

The cyclohexane-1,3-dione derivatives represented by general formula (I) or salts thereof of the present invention have high selectivity between dioctyledons (broad-leaved weeds) and monocotyledons (hardgrass weeds) and in the agricultural scene, thus exhibit a potent herbicidal effect against hardgrass weeds at small dosages under cultivation of broad-leaved crops of leguminous plants including soybeans, cottons, beet, sunflowers, etc. Further in crop rotation of soybeans, wheats, corns, etc., in the case of cultivating soybeans as the second crop of wheats, corns or the like, wheats, corns, etc. grow as volunteer weeds or volunteer corns in soybean fields and greatly affect the growth of soybeans. However, the cyclohexanedione derivatives represented by general formula (I) or salts thereof of the present invention show a potent herbicidal effect also against these volunteer weeds or volunteer corns, as against other hardgrass weeds.

In addition to these purposes, the cyclohexane-1,3-dione derivatives or salts thereof of the present invention can also be utilized as selective controlling agents against hardgrass weeds upon grass cultivation in orchards in which leguminus plants (white clovers, etc.) are used as cover crops. In estate crop cultivation such as oil palms, rubber, etc. in the tropical zone with the southeastern Asia as the central figure, grass cultivation using leguminous weeds as cover crops is remarkably flourished and it is thus also possible to selectively control bladygrasses that grow gregariously and are strongly injurous weeds.

Furthermore, the cyclohexanedione derivatives represented by general formula (I) or salts thereof of the present invention can blight or wither not only barnyardgrass (Echinochloa crus-galli), large crabgrass (Digitaria adscendens), goosegrass (Eleusine indica), wild oat (Avena fatua) and shatter cane (Sorghum bicolor), but hardgrass weeds such as bladygrass (Imperata cylindrica), eulalia (Miscant hus sinensis), ditch reed (Phragmites communis), wild rice (Zizania latifolia) and common reed (Miscanthussacchariflorus) which are said to be controlled only with difficulty, as small dosages over a wide range. Therefore, the cyclohexanedione derivatives of the present invention are selective herbicides which can be utilized over wide areas including non-agricultural fields such as river banks, speedways, normal railroads, parks, etc.

The cyclohexanedione derivatives represented by general formula (I) or salts thereof of the present invention exhibit also a strong herbicidal effect at low dosages not only on hardgrass weeds particularly in the germination period or growth period but also on hardgrass weeds of a height exceeding 1 meter. Furthermore, the cyclohexanedione derivatives represented by general formula (I) or salts thereof also exhibit a strong herbicidal effect at low dosages against annual bluegrass (Poa annual), on which cyclohexanedione type foliar application agents for hardgrass weeds are deemed ineffective.

The cyclohexanedione derivatives represented by general formula (I) or salts thereof of the present invention have high selectivity between dicotyledons (broad-leaved weeds) and monocotyledons (hardgrass weeds) and can thus also be used as non-selective herbicides, in combination with herbicides showing a herbicidal effect against dicotyledons (broad-leaved weeds) in the non-agricultural fields.

The cyclohexanedione derivatives represented by general formula (I) or salts thereof of the present invention are suited for a soil treatment prior to seeding of broad-leaved crops such as soybeans, beets, cottons, sunflowers, etc., a treatment of stalks and leaves in the crop growth period and a soil treatment after seeding but the treatment of stalks and leaves at the growth stage of broad-leaved crops is preferred.

In the case of applying the cyclohexane-1,3-dione derivatives represented by general formula (I) or salts thereof of the present invention as selective herbicides, they are generally made up, according to the customary procedure for preparing agricultural chemicals, into a form convenient to use.

That is, the cyclohexanedione derivatives represented by general formula (I) or salts thereof of the present invention are blended with suitable inert carriers and, if necessary, further with adjuvants, prepared into a suitable form of preparation, e.g., suspension, emulsifiable concentrates, solution, wettable powders, dusts, granules, or tablets through dissolution, dispersion, suspension, impregnation, adsorption, or adhesion, in a suitable ratio.

The inert carriers to be used in the present invention may be either solids or liquids. As examples of the adaptable solid carriers, may be cited vegetable powders such as soybean flour, cereal flour, wood flour, bark flour, saw dust, powdered tobacco stalk, powdered walnut shell, bran, powdered cellulose, extraction residues of vegetables, etc.; fibrous materials such as paper, corrugated paperboard, waste cloth, etc.; synthetic polymers such as powdered synthetic resins, etc.; inorganic or mineral powders such as clays (e.g., kaolin, bentonite, and acid clay), talcs (e.g., talc and pyrophillite), siliceous substances [e.g., diatomaceous earth, silica sand, mica, and white carbon (highly dispersed synthetic silicic acid, also called finely divided hydrated silica or hydrated silicic acid; some commercial products contain calcium silicate as the major constituent)], activated carbon, powdered sulfur, pumice, sintered diatomaceous earth, ground brick, fly ash, sand, calcium carbonate, calcium phosphate, etc.; chemical fertilizers such as ammonium sulfate, ammonium nitrate, urea, ammonium chloride, etc.; and farmyard manure, etc. These materials are used singly or in combination with one another.

The material usable as liquid carriers are selected from those that can be per se solvents and are non-solvent but can disperse the active compounds with the aid of adjuvants. For example, the following materials can be used singly or in combination with one another; water, alcohols (e.g., methanol, ethanol, isopropanol, butanol, ethylene glycol), ketones (e.g., acetone, methyl ethyl ketone, methyl isobutyl ketone, diisobutyl ketone, and cyclohexanone), ethers (e.g., ethyl ether, dioxane, cellosolves, dipropyl ether, and tetrahydrofuran), aliphatic hydrocarbons (e.g., gasoline and mineral oils), aromatic hydrocarbons (e.g., benzene, toluene, xylene, solvent naphtha, and alkylnaphthalenes), halohydrocarbons (e.g., dichloroethane, chlorinated benzenes, chloroform and carbon tetrachloride), esters (e.g., ethyl acetate, diisopropyl phthalate, dibutyl phthalate and dioctyl phthalate), acid amides (e.g., dimethylformamide, diethylformamide, and dimethylacetamide), nitriles (e.g., acetonitrile), dimethyl sulfoxide, etc.

The adjuvants, which are exemplified below, are used according to individual purposes. In some cases, they are used in combination with one another. In some other cases, no adjuvant is used at all.

For purposes of emulsification, dispersion, solubilization and/or wetting of the active compounds, are used surface active agents, for example, polyoxyethylene alkylaryl ethers, polyoxyethylene alkyl ethers, polyoxyethylene higher fatty acid esters, polyoxyethylene resinates, polyoxyethylene sorbitan monooleate, polyoxyethylene sorbitan monooleate, alkylaryl sulfonates, naphthalenesulfonic acid condensation products, lignin sulfonates, and higher alcohol sulfate esters, etc.

For purposes of stabilizing the dispersion, tackificatation, and/or agglomeration of the active compounds, may be used, for example, casein, gelatin, starch, alginic acid, methylcellulose, carboxymethylcellulose, gum arabic, polyvinyl alcohol, turpentine oil, rice bran oil, bentonite, lignin sulfonates, etc.

For purposes of improving the flow property of the solid composition, it is recommendable to use waxes, stearates, alkyl phosphates, etc. As peptizers for a dispersible composition, it is also recommendable to use naphthalenesulfonic acid condensation products, polyphosphates, etc.

It is also possible to add a defoamer such as, for example, a silicone oil, etc.

The content of the active ingredient may be adjusted as occasion demands; for the preparation of powdered or granulated products, it is usually 0.2 to 20% (by weight), and for the preparation of emulsifiable concentrates or wettable powder products, it is desirably 0.1 to 50% (by weight).

For withering various weeds or inhibiting their growth, a weed-destroying dosage or a weed growth-inhibiting dosage of the selective herbicidal composition comprising as the active ingredient the cyclohexane-1,3-dione derivatives or salts thereof of the present invention are applied as such or after properly diluted with or suspended in water or in other suitable medium, to the weeds or to the stalks and leaves or soil of weeds in the area where the emergence or growth of weeds is undesirable.

The amount of the selective herbicidal composition comprising as the active ingredient the cyclohexanedione derivatives or salts thereof of the present invention to be used depends on various factors such as, for example, the purpose of application, objective weeds, the emergence or growth state of weeds and crops, the emergence tendency of weeds, weather, environmental conditions, the form of the herbicidal composition, the mode of application, the type of the field to be treated, the time of application, etc. In applying the herbicidal composition, it is suitable to select the dosage from 1 to 1000 g, preferably 10 to 500 g per 1 hectare, as the active ingredient.

In order to apply the herbicidal composition comprising the cyclohexanedione derivative of the present invention as the active ingredient more broadly to weeds to be controlled and stage to be controlled or in order to reduce the dosage, the herbicidal composition of the present invention can also be blended with other herbicides.

In the case of blending with other herbicides and using as a selective herbicidal blend for soybeans, the cyclohexandione derivatives of the present invention can be blended with herbicides for broad-leaved crops having selectivity to soybeans. Examples of such herbicides include Acifluorfen, Lactofen, Fomesafen, Immazaquim, Bentazone, 2,4-D and MCPB.

Further the non-agricultural fields, the cyclohexanedione derivatives of the present invention can also be used as non-selective herbicides by blending with, for example, Glyphosate, Glyfosinate, Bialaphos or 2,4-D.

The following examples illustrate test examples and formulation examples, but the present invention is not deemed to be limited to these examples.

TEST EXAMPLE 1

Herbicidal Effect On Soybean and Barnyard-grass, Large Crabgrass, Green Foxtail and Shatter Cane of Low-Leaf Stage Plastic pot having a diameter of 12 cm and a height of 12 cm were filled with soil (clay loam) and seeded with soybeans, barnyardgrass (*Echinochloa crusgalli*), large crabgrass (*Digitaria adscendens*), green foxtail (*Setaria viridis*) and shatter cane (*Sorghum bicolor*), respectively, and the seeds were covered with soil at the depth of 1 cm and cultivated in a greenhouse. A designed amount of each test chemical was sprayed to the foliage of the test plants, whereby the plants were in 3-leaved stage. The treatment with each chemical was performed in a spray volume of 1000 liters/ha under a spray pressure of 1 kg/cm² using a spray gun connected with an air compressor. The growth inhibitory rate was evaluated 2 weeks after the chemical treatment by observation with the naked eye, by comparing the results with those on the untreated plants.

The results are shown in Table 3.

TABLE 3

| Compound No. | Dosage (g/ha) | Growth inhibitory rate (%) | | | | |
|---|---|---|---|---|---|---|
| | | Soybean | Barnyard-grass | Large crab-grass | Green foxtail | Shatter cane |
| 1 | 12.5 | 0 | 70 | 60 | 95 | — |
| | 25 | 0 | 100 | 80 | 100 | 100 |
| | 50 | 0 | 100 | 98 | 100 | 100 |
| | 100 | 0 | 100 | 100 | 100 | 100 |
| 3 | 12.5 | 0 | 60 | 50 | 70 | — |
| | 25 | 0 | 95 | 80 | 90 | 95 |
| | 50 | 0 | 100 | 98 | 100 | 98 |
| | 100 | 0 | 100 | 100 | 100 | 100 |
| 4 | 12.5 | 0 | 10 | 60 | 70 | — |
| | 25 | 0 | 80 | 90 | 95 | 85 |
| | 50 | 0 | 95 | 98 | 100 | 98 |
| | 100 | 0 | 100 | 100 | 100 | 100 |
| A | 12.5 | — | 0 | 20 | 40 | — |
| | 25 | — | 20 | 40 | 60 | — |
| | 50 | — | 50 | 70 | 70 | — |
| | 100 | — | 70 | 90 | 98 | — |

Note
— Not tested; The same thing applicable hereinafter.

Compound No. A is Compound No. 79 described in Japanese Patent Application KOKAI (Laid-Open) No. 57-200358, which was provided as a control compound.

Compount No. 79

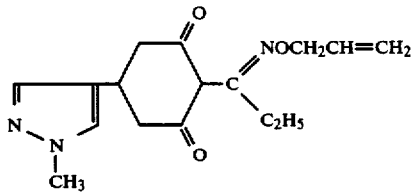

As is noted from the results described above, the compounds of the present invention show selectivity of soybeans in all of the dosages. Compound No. A for control also shows selectivity but the compounds of the present invention exhibit a strong herbicidal effect on barnyardgrass at the dosage of 25 g/ha and the effect is positive even at the dosage of 12.5 g/ha, whereas Compound No. A for control shows the herbicidal effect by 20% at the dosage of 25 g/ha but at the dosage of 12.5 g/ha, shows 0%, indicating poor or no herbicidal effect. Further the compounds of the present invention show a strong herbicidal effect also on large crabgrass and green foxtail at lower dosages, whereas Compound No. A for control does not show a sufficient herbicidal effect. The compounds of the present invention show an excellent herbicidal effect also on shatter cane. From the foregoing results, the compounds of the present invention have selectivity to soybeans and at the same time, exhibit excellent herbicidal effect on various weeds.

TEST EXAMPLE 2

Herbicidal Effect On Barnyardgrass, Large Crabgrass and Green Foxtail of High-Leaf Stage Plastic pots having a diameter of 12 cm and a height of 12 cm were filled with soil and seeded with soybeans, barnyardgrass (*Echinochloa crus-galli*), large crabgrass (*Digitaria adscendens*) and green foxtail (*Setaria viridis*), respectively, and the seeds were covered with the soil at the depth of 1 cm. Then the seeds were cultivated in a greenhouse. A spray mist consisting of designed amount of each test chemical and 1% (V/V) of crop oil was sprayed to the foliage of the test plants, when the leaf age of each test plant reached predetermined leaf-stage mentioned below. The treatment with each chemical was performed by using a spray gun connected to an air compressor at the spray volume of 250 l/ha with an application pressure of 0.8 kg/cm². The growth inhibitory rate was evaluated 2 weeks after the chemical treatment through observation with the naked eye, by comparing the results with those on the untreated plants.

| Weed | Leaf-stage |
|---|---|
| Barnyard grass: | 5 leaf-stage |
| Large crabgrass: | 5 leaf-stage |
| Green foxtail: | 6 leaf-stage |

The results are shown in Table 4.

TABLE 4

| Compound No. | Dosage (g/ha) | Growth inhibitory rate (%) | | | |
|---|---|---|---|---|---|
| | | Soybean | Barnyard-grass | Large crabgrass | Green foxtail |
| 1 | 6.3 | 0 | 98 | 50 | 80 |
| | 12.5 | 0 | 98 | 60 | 90 |
| | 25 | 0 | 100 | 75 | 98 |
| | 50 | 0 | 100 | 80 | 98 |
| | 100 | 0 | 100 | 90 | 100 |
| 2 | 6.3 | 0 | 90 | 80 | 90 |
| | 12.5 | 0 | 98 | 90 | 95 |
| | 25 | 0 | 100 | 95 | 95 |
| | 50 | 0 | 100 | 98 | 100 |
| | 100 | 0 | 100 | 98 | 100 |
| 3 | 6.3 | 0 | 80 | 70 | 85 |
| | 12.5 | 0 | 90 | 80 | 90 |
| | 25 | 0 | 100 | 80 | 99 |
| | 50 | 0 | 100 | 85 | 100 |
| | 100 | 0 | 100 | 90 | 100 |
| 4 | 6.3 | 0 | 80 | 60 | 70 |
| | 12.5 | 0 | 90 | 70 | 85 |
| | 25 | 0 | 100 | 90 | 98 |
| | 50 | 0 | 100 | 90 | 98 |
| | 100 | 0 | 100 | 95 | 100 |
| A | 6.3 | — | 50 | 40 | 60 |
| | 12.5 | — | 70 | 60 | 70 |
| | 25 | — | 98 | 70 | 85 |
| | 50 | — | 100 | 80 | 95 |
| | 100 | — | 100 | 85 | 99 |

As is noted from the results described above, the compounds of the present invention exhibit a strong herbicidal effect on weeds in the high leaf stage, for example, on barnyardgrass at the dosage of 12.5 g/ha and the effect is positive even at the dosage of 6.3 g/ha, whereas Compound No. A for control does not show a sufficient herbicidal effect. Further the compounds of the present invention shows a strong herbicidal effect on large crabgrass at the dosage of 50 g/ha. However, Compound No. A for control does not show a sufficient herbicidal effect at the same dosage. Furthermore, the compounds of the present invention shows a sufficient herbicidal effect on green foxtail even at the dosage of 12.5 g/ha, whereas Compound No. A for control does not show a sufficient herbicidal effect at the same dosage. These results reveal that the compounds of the present invention exhibit an excellent herbicidal effect on various weeds.

Based on the results described above, $ED_{90}$ of the compounds according to the present invention and Compound No. A for large crabgrass and green foxtail was calculated by probit conversion.

The results are shown in Table 5.

TABLE 5

| Compound No. | $ED_{90}$ for green foxtail amount of active ingredient (g/ha) | $ED_{90}$ for large crabgrass amount of active ingredient (g/ha) |
| --- | --- | --- |
| 1. | 11.8 | 111.1 |
| 2. | 5.4 | 13.7 |
| 3. | 9.6 | 116.0 |
| 4. | 15.2 | 42.7 |
| A. | 31.8 | 140.5 |

It is noted also from the results described above that the compounds of the present invention show a potent herbicidal effect on large crabgrass and green foxtail at low dosage, as compared to the comparative compound

TEST EXAMPLE 3

Herbicidal Effect On Wheat, Wild Oat and Annual Bluegrass

Plastic pots having a diameter of 12 cm and a height of 12 cm were filled with soil and seeded with wheat (*Triticum aestivum*), wild oat (*Avena fatuas*) and annual bluegrass (*Poa annua*) which were volunteer weeds, respectively, and the seeds were covered with the soil at the depth of 1 cm.

Then the seeds were cultivated in a greenhouse. A designed amount of each test chemical was sprayed to the foliage of the test plants, when the leaf reached 2-leaved stage. The treatment with each chemical was performed in a manner similar to Test Example 1. The growth inhibitory rate was evaluated 4 weeks after the chemical treatment through observation with the naked eye, by comparing the results with those on the untreated plants The results are shown in Table 6.

TABLE 6

| Compound No. | Dosage (g/ha) | Growth inhibitory rate (%) | | |
| --- | --- | --- | --- | --- |
| | | Wheat | Wild Oat | Annual bluegrass |
| 1 | 12.5 | — | 40 | — |
| | 25 | — | 70 | — |
| | 50 | 70 | 95 | 70 |
| | 100 | 100 | 100 | 95 |
| 3 | 12.5 | — | 30 | — |
| | 25 | — | 50 | — |
| | 50 | 60 | 90 | 60 |
| | 100 | 90 | 95 | 90 |
| 4 | 12.5 | — | 30 | — |
| | 25 | — | 60 | — |
| | 50 | 50 | 90 | 60 |
| | 100 | 100 | 98 | 90 |
| A | 12.5 | — | 0 | — |
| | 25 | — | 30 | — |
| | 50 | 40 | 70 | 30 |

TABLE 6-continued

| Compound No. | Dosage (g/ha) | Growth inhibitory rate (%) | | |
| --- | --- | --- | --- | --- |
| | | Wheat | Wild Oat | Annual bluegrass |
| | 100 | 60 | 80 | 60 |

As is noted from the results described above, the compounds of the present invention show a herbicidal effect on wheat as volunteer weeds by 70% at the dosage of 50 g/ha and by 100% at the dosage of 100 g/ha, whereas Compound No. A for control shows the effect merely by 40% and 60% at the same dosages, respectively. The compounds of the present invention show a strong herbicidal effect on wild oat at the dosage of 50 g/ha and the effect is still positive even at the dosage of 25 g/ha; whereas Compound No. A for control shows a poor herbicidal effect merely by 70% at the dosage of 50 g/ha and by 30% at the dosage of 12.5 g/ha. Likewise, the compounds of the present invention show as strong herbicidal effect as 95% on annual bluegrass at the dosage of 100 g/ha and the effect is still more than 70% even at the dosage of 25 g/ha; whereas Compound No. A for control does not show any satisfactory herbicidal effect, by 60% at the dosage of 100 g/ha and by 30% at the dosage of 50 g/ha.

TEST EXAMPLE 4

Herbicial Effect On Johnsongrass, Quack-Grass, Bermudagrass and Bladygrass

Rhizomes of Johnsongrass (*Sorghum halepense*), bermudagrass (*Cynodon dactylon*) and bladygrass (*Imperate cylindrica*), which were uniformly germinated, were transplanted to plastic pots having a diameter of 12 cm and a height of 12 cm filled with soil and covered with the soil at the depth of 1 cm. Then the rhizomes were cultivated in a greenhouse. After the aerial part reached a desired growth stage, each herbicidal composition comprising the compounds of the present invention as the active ingredient was sprayed to the foliage of the test plants. The treatment with each chemical was performed in a manner similar to Test Example 1. The growth inhibitory rate was evaluated 3 weeks after the chemical treatment through observation with the naked eye, by comparing the results with those on the untreated plants.

The results are shown in Table 7.

TABLE 7

| Compound No. | Dosage (g/ha) | Growth inhibitory rate (%) | | | | |
| --- | --- | --- | --- | --- | --- | --- |
| | | Johnson grass | Quack-grass | Large bermuda-grass | Blady-grass | Soybean |
| 1 | 12.5 | — | 50 | 40 | — | 0 |
| | 25 | — | 90 | 75 | — | 0 |
| | 50 | — | 90 | 80 | 75 | 0 |
| | 100 | 100 | 100 | 95 | 75 | 0 |
| | 200 | 100 | — | — | — | 0 |
| 3 | 12.5 | — | 50 | 40 | — | 0 |
| | 25 | — | 65 | 45 | — | 0 |
| | 50 | — | 70 | 80 | 70 | 0 |
| | 100 | 95 | 100 | 85 | 75 | 0 |
| | 200 | 100 | — | — | — | 0 |
| 4 | 12.5 | — | 30 | 40 | — | 0 |
| | 25 | — | 70 | 75 | — | 0 |
| | 50 | — | 90 | 85 | 80 | 0 |
| | 100 | 100 | 100 | 100 | 80 | 0 |
| | 200 | 100 | | | | 0 |
| A | 12.5 | — | 5 | 10 | — | — |
| | 25 | — | 20 | 10 | — | — |
| | 50 | — | 45 | 10 | — | — |

TABLE 7-continued

| Com-pound No. | Dosage (g/ha) | Growth inhibitory rate (%) | | | | |
|---|---|---|---|---|---|---|
| | | Johnson grass | Quack-grass | Large bermuda-grass | Blady-grass | Soybean |
| | 100 | 85 | 80 | 45 | — | — |
| | 200 | 100 | — | — | — | — |

As is noted from the results described above, the compounds of the present invention show a strong herbicidal effect, for example, on Johnsongrass by 95% or more at the dosage of 100 g/ha; whereas Compound No. A for control does not show any satisfactory herbicidal effect at the same dosage. The compounds of the present invention show a strong herbicidal effect on quackgrass at the dosage of 25 g/ha and the strong herbicidal effect is still exhibited even at the dosage of 12.5 g/ha; whereas Compound No. A for control shows a herbicidal effect merely by 20% at the dosage of 25 g/ha and at the dosage of 12.5 g/ha, the effect is as low as 5% which hardly shows the herbicidal effect. Further, the compounds of the present invention show a sufficient herbicidal effect on bermudagrass even at the dosage of 50 g/ha; whereas Compound No. A for control shows a herbicidal effect merely by 10% at the same dosage. Furthermore, the compounds of the present invention shows an excellent herbicidal effect also on bladygrass.

The foregoing results reveal that the compounds of the present invention show an excellent herbicidal effect on various weeds such as Johnsongrass, quackgrass, bermudagrass, bladygrass, etc. at low dosages and have selective to soybeans even at high dosage.

TEST EXAMPLE 5

Herbicidal Effect On Corn

Plastic pots having a diameter of 12 cm and a height of 12 cm were filled with soil and seeded with corn (Zea mats) and the seeds were covered with the soil at the depth of 1 cm. Then the seeds were cultivated in a greenhouse. After the leaf age reached 3-leaf stage, each herbicidal composition comprising the compounds of the present invention as the active ingredient was sprayed to the foliage of the test plants. The treatment with each chemical was performed in a manner similar to Test Example 1. The growth inhibitory rate was evaluated 2 weeks after the chemical treatment through observation with the naked eye, by comparing the results with those on the untreated plants.

The results are shown in Table 8.

TABLE 8

| Compound No. | Dosage (g/ha) | Growth inhibitory rate (%) Corn |
|---|---|---|
| 1 | 25 | 90 |
| | 50 | 100 |
| | 100 | 100 |
| 2 | 25 | 100 |
| | 50 | 100 |
| | 100 | 100 |
| 3 | 25 | 95 |
| | 50 | 100 |
| | 100 | 100 |
| 4 | 25 | 100 |
| | 50 | 100 |
| | 100 | 100 |
| A | 25 | 70 |
| | 50 | 80 |

TABLE 8-continued

| Compound No. | Dosage (g/ha) | Growth inhibitory rate (%) Corn |
|---|---|---|
| | 100 | 100 |

From the results described above, the compounds of the present invention show a herbicidal effect as strong as 90% or more at the dosage of 50 g/ha; whereas Compound No. A for control shows a herbicidal effect by 80% at the same dosage but does not show any satisfactory and sufficient herbicidal effect.

FORMULATION EXAMPLE 1

A wettable powder composition obtained by uniformly mixing and grinding the following components.
Compound No 1: 50 parts
Mixture of clay and white carbon wherein clay is the major constituent: 45 parts
Polyoxyethylene nonylphenyl ether: 5 parts

FORMULATION EXAMPLE 2

A granule composition obtained by uniformly mixing and grinding the following components, kneading the mixture with a suitable amount of water, and granulating the kneaded mixture.
Compound No. 2: 5 parts
Mixture, of bentonite and clay: 90 parts
Calcium lignuninsulfonate: 5 parts

FORMULATION EXAMPLE 3

An emulsifiable concentrate obtained by uniformly mixing the following components.
Compound No. 3: 50 parts
Xylene: 40 parts
Mixture of polyoxyethylene nonylphenyl ether and calcium alkylbenzenesulfonate: 10 parts While the invention has been described in detail, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A cyclohexane-1,3-dione derivative represented by general formula (I):

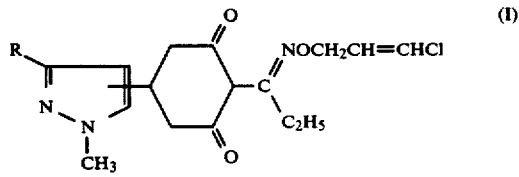

wherein R represents a hydrogen atom or a methyl group and the cyclohexane ring is substituted at the 4- or 5-position of the pyrazole ring, or salts thereof.

2. A compound or a salt thereof as claimed in claim 1 wherein R is a hydrogen atom.

3. A compound or a salt thereof as claimed in claim 2 which is selected from the following compounds:
2-{1-(3-Chloro-2-propenyloxyimino)propyl}-5-(1-methyl-1H-pyrazol-4-yl)cyclohexane-1,3-dione,
2-{1-(3-Chloro-2-propenyloxyimino)propyl}-5-(1-methyl-1H-pyrazol-5-yl)cyclohexane-1,3-dione, (E)-2-{1-(3-Chloro-2-propenyloxyimino)propyl}-5-1-methyl-1H-pyrazol-4-yl)cyclohexane-1,3-dione, and (E)-2-{1-(3-Chloro-2-propenyloxyimino)propyl}-5-(1-methyl-1H-pyrazol-5-yl)cyclohexane-1,3-dione.

4. A compound or a salt thereof as claimed in claim 1 wherein R is a methyl group.

5. A compound or a salt thereof as claimed in claim 4 which is selected from the following compounds:
2-{(3-Chloro-2-propenyloxyimino)propyl}-5-(1,3-dimethyl-1H-pyrazol-4-cyclohexane-1,3-dione,
2-{(3-Chloro-2-propenyloxyimino)propyl}-5-(1,3-dimethyl-1H-pyrazol-5-cyclohexane-1,3-dione,
(E)-2-{1-(3-Chloro-2-propenyloxyimino)propyl}-5-(1,3-dimethyl-1H-pyrazol-4-yl)cyclohexane-,3-dione, and
(E)-2-{1-(3-Chloro-2-propenyloxyimino)propyl}-5-(1,3-dimethyl-1H-pyrazol-5-yl)cyclohexane-1,3-dione.

6. A selective herbicidal composition comprising a cyclohexane-1, 3-dione derivative represented by general formula (I):

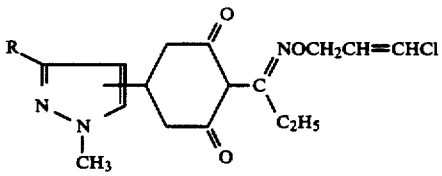

wherein R represents a hydrogen atom or a methyl group and the cyclohexane ring is substituted at the 4- or 5-position of the pyrazole ring, or salts thereof in an herbicidally effective amount and an inert carrier.

7. A selective herbicidal composition as claimed in claim 6 which is for applying to crop soybeans.

8. A selective herbicidal composition as claimed in claim 7 which is used to treat soybeans at the post-emergence stage.

9. A selective herbicidal composition as claimed in claim 8 which is selected from the following compounds and salts thereof:
2-{1-(3-Chloro-2-propenyloxyimino)propyl}-5-(1-methyl-1H-pyrazol-4-yl)cyclohexane-1,3-dione,
2-{1-(3-Chloro-2-propenyloxyimino)propyl}-5-(1-methyl-1H-pyrazol-5-yl)cyclohexane-1,3-dione,
(E)-2-{1-(3-Chloro-2-propenyloxyimino)propyl}-5-(1-methyl-1H-pyrazol-4-yl)cyclohexane-1,3-dione,
(E)-2-{1-(3-Chloro-2-propenyloxyimino)propyl}-5-(1-methyl-1H-pyrazol-5-yl)cyclohexane-1,3-dione,
2-{1-(3-Chloro-2-propenyloxyimino)propyl}-5-(1,3-dimethyl-1H-pyrazol-4-yl)cyclohexane-1,3-dione,
2-{1-(3-Chloro-2-propenyloxyimino)propyl}-5-(1,3-dimethyl-1H-pyrazol-5-yl)cyclohexane-1,3-dione,
(E)-2-{1-(3-Chloro-2-propenyloxyimo)propyl}-5-(1,3-dimethyl-1H-pyrazol-4-yl)cyclohexane-1,3-dione, and,
(E)-2-{1-(3-Chloro-2-propenyloxyimino)propyl}-5-(1,3-dimethyl-1H-pyrazol-5-yl)cyclohexane-1,3-dione.

10. A method for controlling weeds which comprises applying as an active ingredient a cyclohexane-1,3-dione derivative represented by general formula (I):

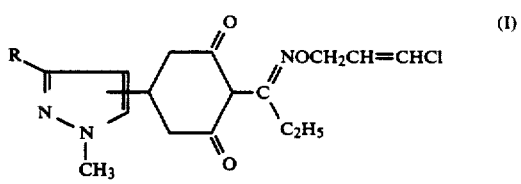

wherein R represents a hydrogen atom or a methyl group and the cyclohexane ring is substituted at the 4- or 5-position of the pyrazole ring, or salts thereof, in a herbicidally effective amount of 1 to 1000 g/hectare.

11. A method for controlling weeds as claimed in claim 10 wherein said active ingredient is selected from the following compounds and salts thereof:
2-{1-(3-Chloro-2-propenyloxyimino)propyl}-5-(1-methyl-1H-pyrazol-4-yl)cyclohexane-1,3-dione,
2-{1-(3-Chloro-2-propenyloxyimino)propyl}-5-(1-methyl-1H-pyrazol-5-yl)cyclohexane-1,3-dione,
(E)-2-{1-(3-Chloro-2-propenyloxyimino)propyl}-5-(1-methyl-1H-pyrazol-4-yl)cyclohexane-1,3-dione,
(E)-2-{1-(3-Chloro-2-propenyloxyimino)propyl}-5-(1methyl-1H-pyrazol-5-yl)cyclohexane-1,3-dione,
2-{1-(3-Chloro-2-propenyloxyimino)propyl}-5-(1,3-dimethyl-1H-pyrazol-4-yl)cyclohexane-1,3-dione,
2-{1-(3-Chloro-2-propenyloxyimino)propyl}-5-(1,3-dimethyl-1H-pyrazol-5-yl)cyclohexane-1,3-dione,
(E)-2-{1-(3-Chloro-2-propenyloxyimino)propyl}-5-(1,3-dimethyl-1H-pyrazol-4-yl)cyclohexane-1,3-dione, and,
(E)-2-{1-(3-Chloro-2-propenyloxyimino)propyl}-5-(1,3-dimethyl-1H-pyrazol-5-yl)cyclohexane-1,3-dione.

* * * * *